United States Patent [19]

Kreighbaum et al.

[11] 4,343,940

[45] Aug. 10, 1982

[54] ANTI-TUMOR QUINAZOLINE COMPOUNDS

[75] Inventors: William E. Kreighbaum; William T. Comer, both of Evansville, Ind.

[73] Assignee: Mead Johnson & Company, Evansville, Ind.

[21] Appl. No.: 241,317

[22] Filed: Mar. 6, 1981

Related U.S. Application Data

[63] Continuation-in-part of Ser. No. 11,819, Feb. 13, 1979, Pat. No. 4,314,943.

[51] Int. Cl.$^3$ ............... C07D 405/12; A61K 31/505; C07D 405/14
[52] U.S. Cl. .................... 544/283; 424/251; 544/313; 544/287; 548/309
[58] Field of Search ........................ 544/283

[56] References Cited

U.S. PATENT DOCUMENTS 3,298,291  4/1966  Minielli et al. ............... 544/283
3,455,920  7/1969  Yale ............................ 544/289
3,637,693  1/1972  Otterstedt et al. ............ 544/283

FOREIGN PATENT DOCUMENTS 773818  4/1972  Belgium.
844136  11/1976  Belgium.

OTHER PUBLICATIONS

Derwent No. 29,765, South African 67/3220, 9/29/67 (2/1).
Derwent No. 46879w/28, Japan 5-0030-890 23, 3/27/75 (2/4).
Bradner, Cancer and Chemotherapy, vol. 1, 1980, pp. 221–227 (4/11).
Taylor, et al., "Chemical Abstracts", vol. 80, 1974, col. 47718g.

*Primary Examiner*—Donald G. Daus
*Assistant Examiner*—James H. Turnipseed
*Attorney, Agent, or Firm*—Robert H. Uloth; Robert E. Carnahan

[57] ABSTRACT

4-Ethyl-6-methoxy-7-(oxiranylmethoxy)quinazoline and its isomer 4-ethyl-7-methoxy-6-(oxiranylmethoxy)-quinazoline have potent anti-tumor activity in animals.

3 Claims, No Drawings

ANTI-TUMOR QUINAZOLINE COMPOUNDS

REFERENCE TO RELATED APPLICATION

This application is a continuation-in-part of co-pending application Ser. No. 011,819 filed February 13, 1979 now U.S. Pat. No. 4,314,943. Procedures 35, 36, 37, and 38 of Ser. No. 011,819 are identical with Procedures 1, 2, 3, and 4 hereof.

FIELD OF THE INVENTION

The invention is concerned with heterocyclic carbon compounds of the quinazoline series (Class 544, Subclass 253) having oxirane-containing substituent groups.

DESCRIPTION OF THE PRIOR ART

The following are referred to as representative of cytostatic compounds known in the prior art which bear the oxirane substituent. None of these is believed to be structurally related to the present compounds in such a way as to raise a presumption of obviousness. The Derwent Publications, Ltd., London WC1X 8RP England, Farmdoc Accession Numbers relative to the abstracts of the patents cited are used for reference purposes.

Derwent No. 29,765, South African No. 67/3220 published Sept. 29, 1967, 5,5-Dimethyl-1,3-di(oxiranylmethyl)imidazolidine-2,4-dione is useful as an antitumor agent.

Derwent No. 46879 W/28, Japan No. 5 0030 890 23 published Mar. 27, 1975, 5-Fluoro-1-(oxiranylmethyl)-2,4-(1$\underline{H}$,3$\underline{H}$)pyrimidindione has anti-carcinogenic activity.

Belgian No. 844,136 published Nov. 3, 1976, (Derwent No. 88859 X/48) 5-Fluoro-2-(oxiranylmethoxy)-4-oxopyrimidine is alleged to be a low toxicity anti-tumor agent.

Quinazoline compounds, also structurally unrelated to the present substances, have been reported to possess anti-tumor activity. The following are illustrative.

Belgium No. 773,818 (Derwent No. 25523Y), published Apr. 12, 1972, Quinazolone diurethanes such as 3-methyl-6-(methoxycarbonylamino)-2-[3-(methoxycarbonylamino)phenyl]quinazolin-4(3$\underline{H}$)-one are effective against the mouse L1210 leukemia, pages 1, 7, 8, 9, 10, and 21.

U.S. Pat. No. 3,455,920 patented July 15, 1969 (Derwent No. 38866), 6-Nitro-2-phenyl-1,2,3,4-tetrahydroquinazolin-4-one exhibits cytotoxic activity in vivo against the Walker 256 carcinoma in mice.

Numerous entries appear in Chemical Abstracts Formula Index under the molecular formula $C_{11}H_{10}N_2O_2$ which corresponds to the quinazoline ring substituted by the (2-oxiranyl)methoxy group, but no compound is indexed having the (2-oxiranyl)methoxy group attached to the quinazoline ring. The most closely related compounds of this formula which is reported is 3-[(2-oxiranyl)methyl]-1,4-dihydro-(4$\underline{H}$)-quinazolin-4-one, which structure differs in a number of significant respects from the present compounds.

SUMMARY OF THE INVENTION

This invention is concerned with quinazoline compounds having the following structural formula

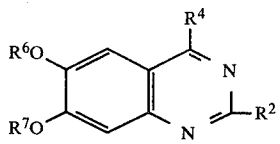

Formula I

In Formula I at least one of $R^6$ and $R^7$ is the oxiranylmethyl group and the other is methyl or a second oxiranylmethyl group. $R^2$ and $R^4$ are independently selected from hydrogen, alkyl having 1 to 5 carbon atoms, phenyl, substituted phenyl, phenylalkyl having up to 8 carbon atoms, substituted phenylalkyl having up to 8 carbon atoms apart from the substituents. The substituents of the substituted phenyl and substituted phenylalkyl groups are ring attached and there may be one or two of them. They are selected from halogen including chlorine, bromine, iodine, and fluorine, methyl, or methoxy groups.

The compounds of Formula I which are described in Procedures 3 and 4 hereof, namely, those wherein $R^2$ is hydrogen, $R^4$ is ethyl, and one of $R^6$ and $R^7$ is oxiranylmethyl and the other is methyl, have utility as intermediates in the preparation of antihypertensive agents as described in our prior co-pending application Ser. No. 011,819. These compounds also have antithrombogenic, hypotensive, ileal relaxant, and smooth muscle relaxant activity, the latter similar to that exhibited by bronchodilator agents. The compound of Procedure 4 inhibits the passive cutaneous anaphylaxis reaction in the rat suggestive of anti-allergy activity.

The quinazoline compounds of this invention have antitumor activity against transplanted animal tumors of established utility for the screening of anticancer agents. The tumors against which the present substances are active include the ascitic tumors P388 and L1210 leukemia which are widely used for primary screening and the B16 melanoma and Lewis Lung carcinoma which are used in secondary screening. A review of the screening strategy with an enumeration of the transplanted animal tumors employed has been published by William T. Bradner in Cancer and Chemotherapy, Vol. 1, pages 221-227 (1980).

Generally, the screening method involves administering a standardized tumor innoculum by intraperitoneal injection to the test animals arranged into groups to which various doses of test compound are administered by intraperitoneal injection, and median survival times in days for the various groups are determined. The results are then expressed as the percent T/C which is the ratio of the median survival time (MST) for the group of treated animals to the MST of the untreated control animals multiplied by 100. Any compound exhibiting a percent T/C≧125 is considered to have significant antitumor activity. Various dosage schedules may be employed such as a single dose on day 1 (d.1), three doses individually on days 1, 5, and 9 after innoculation (d.1, 5, and 9), daily dosage over a period of time such as for nine days (qd.1→9), or others as may be suitable. The following results were obtained with the compounds of Procedures 3 and 4 hereof which were administered suspended in DMSO/saline or aqueous hydroxypropylcellulose.

| Compound of Procedure 3 P388 Leukemia | | | | | |
|---|---|---|---|---|---|
| Treatment Schedule | Dose, IP mg/kg/inj | MST Days | Effect MST % T/C | Average Weight Change, g | Survivors Day 6 |
| d.1 | 150 | TOX | TOX | TOX | 0/6 |
|  | 100 | 14.5 | 145 | −1.1 | 6/6 |
|  | 50 | 13.0 | 130 | +0.3 | 6/6 |
|  | 25 | 11.5 | 115 | +1.2 | 6/6 |
| d.1, 5&9 | 100 | 17.0 | 170 | −2.3 | 6/6 |
|  | 50 | 13.5 | 135 | −0.4 | 5/6 |
|  | 25 | 12.0 | 120 | +0.6 | 6/6 |
|  | 12.5 | 10.0 | 100 | +1.3 | 6/6 |
| qd 1→9 | 25 | 15.0 | 150 | −0.7 | 6/6 |
|  | 12.5 | 13.0 | 130 | +0.5 | 6/6 |
|  | 6.25 | 11.0 | 110 | +0.9 | 6/6 |
|  | 3.13 | 9.5 | 95 | +2.1 | 6/6 |
|  | Saline | 10.0 | — | +2.6 | 10/10 |

Tumor inoculum: 10⁶ ascites cells implanted i.p.
Host: CDF₁ ♀ mice.
TOX: <4/6 mice alive on Day 6

| Compound of Procedure 4 P388 Leukemia | | | | | |
|---|---|---|---|---|---|
| Treatment Schedule | Dose, IP mg/kg | MST Days | Effect MST % T/C | Average Weight Change, g | Survivors Day 5(30) |
| d.1 | 100 | TOX | TOX | −3.7 | 2/4 |
|  | 50 | 12.5 | 139 | −3.0 | 4/4 |
|  | 25 | 12.0 | 133 | −2.3 | 4/4 |
|  | 12.5 | 11.0 | 122 | −1.1 | 4/4 |

Tumor inoculum: 10⁶ ascites cells implanted ip.
Host: CDF₁ ♀ mice.
TOX: <4/6 or 3/4 mice alive on Day 5.

| Compound of Procedure 3 L1210 Leukemia | | | | | |
|---|---|---|---|---|---|
| Treatment Schedule | Dose, IP mg/kg/day | MST Days | Effect MST % T/C | Average Weight Change, g | Survivors Day 5 |
| d.1 | 120 | 11.0 | 183 | −3.7 | 6/6 |
|  | 80 | 10.5 | 175 | −2.3 | 6/6 |
|  | 40 | 9.0 | 150 | −0.9 | 5/6 |
|  | 20 | 8.0 | 133 | −1.0 | 5/6 |
| d.1, 5&9 | 120 | 9.5 | 158 | −3.4 | 4/6 |
|  | 80 | 9.0 | 150 | −1.0 | 5/5 |
|  | 40 | 7.0 | 117 | +0.2 | 5/6 |
|  | 20 | 8.0 | 133 | +0.2 | 5/6 |
| qd 1→9 | 60 | 9.0 | 150 | −3.2 | 6/6 |
|  | 40 | 10.0 | 167 | −2.8 | 6/6 |
|  | 20 | 9.5 | 158 | −1.1 | 6/6 |
|  | 10 | 8.5 | 142 | −0.8 | 6/6 |
|  | Saline | 6.0 | — | +1.4 | 10/10 |

Tumor inoculum: 10⁶ ascites cells implanted i.p.
Host: CDF₁ ♀ mice.

| Compound of Procedure 3 B16 Melanoma | | | | | |
|---|---|---|---|---|---|
| Treatment Schedule | Dose, IP mg/kg/inj | MST Days | Effect MST % T/C | Average Weight Change, g | Survivors Day 10(60) |
| d.1, 5&9 | 120 | TOX | TOX | −3.5 | 5/10 |
|  | 80 | 41.0 | 178 | −1.7 | 9/10 (2)* |
|  | 40 | 35.0 | 152 | −0.2 | 10/10 |
|  | 20 | 29.5 | 128 | −0.3 | 10/10 |
| gd 1→9 | 60 | 30.0 | 130 | −2.4 | 10/10 |
|  | 40 | 36.5 | 159 | −2.1 | 10/10 (3)* |
|  | 20 | 36.0 | 156 | −1.8 | 10/10 |
|  | 10 | 31.0 | 135 | −1.0 | 10/10 |

-continued

| Compound of Procedure 3 B16 Melanoma | | | | | |
|---|---|---|---|---|---|
| Treatment Schedule | Dose, IP mg/kg/inj | MST Days | Effect MST % T/C | Average Weight Change, g | Survivors Day 10(60) |
| | Saline | 23.0 | — | +2.3 | 10/10 |

*Tumor-free at autopsy as determined by visual inspection.
Tumor inoculum: 0.5 ml of a 10% brei, ip
Host: BDF₁ ♀ mice.
TOX: <7/10 mice alive on d.10.

| Compound of Procedure 3 Lewis Lung Carcinoma | | | | | |
|---|---|---|---|---|---|
| Treatment Schedule | Dose, IP mg/kg/inj | MST Days | Effect MST % T/C | Average Weight Change, g | Survivors Day 10(60) |
| d.1, 5&9 | 80 | >60.0 | >400 | −0.8 | 10/10 (6)* |
|  | 60 | >60.0 | >400 | −0.5 | 10/10 (6)* |
|  | 40 | 20.0 | 133 | −0.5 | 10/10 (4)* |
| qd 1→9 | 60 | 19.0 | 127 | −2.0 | 8/10 (3)* |
|  | 40 | >60.0 | >400 | −1.4 | 10/10 (7)* |
|  | 20 | 20.0 | 133 | −0.5 | 10/10 (3)* |
|  | Saline | 15.0 | — | −0.4 | 10/10 |

*Tumor-free.
Tumor inoculum: 10⁶ tumor brei cells, ip
Host: BDF₁ ♀ mice.
TOX: <7/10 mice alive on d.10.

DETAILED DESCRIPTION OF THE INVENTION

The compounds of the present invention are prepared by reaction of an intermediate of Formula II wherein $R^2$ and $R^4$ are as previously defined, one of $R^a$ and $R^b$ is hydrogen, and the other of $R^a$ and $R^b$ is hydrogen, or methyl, with epichlorohydrin or epibromohydrin in the presence of a base.

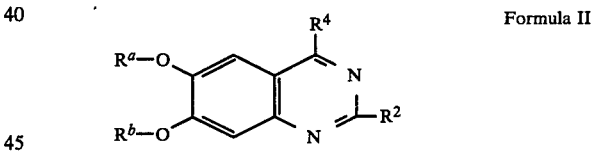

Formula II

A reaction inert organic liquid reaction medium is employed at a temperature of from about 25° C. up to about 150° C. Suitable bases include sodium and potassium hydroxides, alkoxides, and carbonates. Suitable reaction inert liquid organic media include ethanol, propanol, butanol, dibutyl ether, tetrahydrofuran, benzene, toluene, dimethylsulfoxide, dimethylformamide, dimethylacetamide, ethylene glycol dimethyl ether, ethylene glycol monomethyl ether, hexamethyl phosphoramide, and other alkanols, ethers, and hydrocarbons. A reaction medium in which the reactants are soluble is preferred. Use of a crown ether catalyst such as 18-crown-6 is sometimes advantageous. The preferred system employs finely powdered potassium carbonate as base in dimethylsulfoxide as reaction medium, with epibromohydrin as reactant at a reaction temperature of about 25° C. as described in Procedure 3 below.

The intermediates of Formula II are prepared by methods known in the art, for instance by catalytic debenzylation of the corresponding compound of Formula II wherein one or both of $R^a$ and $R^b$ is the benzyl group. The latter are produced from the corresponding alkylphenones of Formula III wherein one of $R^c$ and $R^d$ is benzyl and the other is methyl or benzyl.

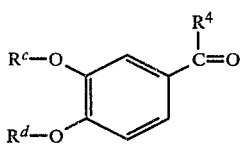

Formula III

Those substances of Formula III wherein $R^c$ is benzyl and $R^d$ is methyl are prepared from 2-methoxyphenol by conversion thereof to the chloroacetate ester, acylation thereof with an acid of the Formula $R^4CO_2H$ in the presence of polyphosphoric acid, hydrolysis of the chloroacetate ester to yield the corresponding 1-(3-hydroxy-4-methoxyphenyl)phenone, and benzylation of the latter to yield the corresponding substances of Formula III wherein $R^c$ is benzyl and $R^d$ is methyl. This is illustrated in Procedure 2 below.

Those intermediates of Formula III wherein $R^c$ is methyl, and $R^d$ is benzyl are prepared by acylation of 2-methoxyphenol with a carboxylic acid of the formula $R^4CO_2H$ in the fashion referred to above followed by benzylation of the corresponding 3-methoxy-4-hydroxyphenone to yield the compound of Formula III wherein $R^c$ is methyl, and $R^d$ is benzyl.

The intermediates of Formula III are converted to those of Formula II by conventional means for the synthesis of quinolines such as are illustrated in U.S. Pat. No. 3,248,292 patented Apr. 26, 1966. The last step is removal of the benzyl group represented by $R^c$ or $R^d$ in Formula III to yield the corresponding hydroxyl compound of Formula II.

An alternative method for production of the intermediates of Formula II wherein $R^a$ is methyl, and $R^b$ is hydrogen or $R^a$ and $R^b$ are each hydrogen atoms is by hydrolysis of the corresponding compound wherein $R^a$ and $R^b$ are each methyl with concentrated aqueous hydrobromic acid at the reflux temperature as is illustrated in Procedures 1 and 5 hereof.

DESCRIPTION OF SPECIFIC EMBODIMENTS

In the following procedures, temperatures are expressed in degrees centigrade (°). Melting points are corrected values according to the U.S.P. method where indicated (corr.). Abbreviations employed are MeOH (methanol), DMSO (dimethylsulfoxide), i-PrOH (isopropanol), abs.EtOH (absolute ethanol), EtOAc (ethyl acetate), EtOH (95% ethanol), Et$_2$O (diethyl ether), THF (tetrahydrofuran), MEK (2-butanone), i-PrOAc (isopropyl acetate), i-Pr$_2$O (di-isopropyl ether), AcOH (acetic acid), TLC (thin layer chromatography), d (decomposition). Other abbreviations have conventional established meanings.

Procedure 1. 4-ETHYL-6-METHOXYQUINAZOLIN-7-OL.—A solution of 100 g. (0.46 mole) of 4-ethyl-6,7-dimethoxyqunazoline (CAS Registry No. 4015-32-1, m.p. 146°–148°) in 250 ml. of 48% hydrobromic acid was refluxed 3.5 hrs. at which time only a trace of this starting material was evident by TLC (9:1 CHCl$_3$-MeOH; silica). The mixture was cooled to 25° and neutralized (pH 7) with concentrated NH$_4$OH. After the suspension had been chilled overnight (5°), the crude grey-green precipitate was collected on a filter and dried—first overnight in air and then in a vacuum oven at 50°/60 mm for 18 hrs. The dry solid (70 g., m.p. 210°–215°) was recrystallized from MeOH-(i-Pr)$_2$O to give 42 g. (43%) of chartreuse powder, m.p. 221°–224° (uncorr.). The identity of the product was confirmed by examination of the IR spectrum.

Procedure 2. 4-ETHYL-7-METHOXYQUINAZOLIN-6-OL.—2-Methoxyphenol was esterified by reaction with chloroacetyl chloride to give in 75% yield, 2-methoxyphenyl chloroacetate, m.p. 60°–61.5°. This material was acylated with propionic acid in the presence of polyphosphoric acid to produce 2-methoxy-5-propionylphenyl chloroacetate in 75% yield, m.p. 77°–79.5° C. This ester was hydrolyzed with sodium acetate in methanol to yield 1-(3-hydroxy-4-methoxyphenyl)-1-propanone, m.p. 91°–92°, yield 90%. Benzylation of the later by treatment in acetone with benzyl chloride and potassium carbonate yielded 1-(3-benzyloxy-4-methoxyphenyl)-1-propanone, m.p. 83°–85°, yield 96%. The latter was then nitrated by treatment with 1:3 nitric acid/acetic acid at 18°–20° to yield 1-(2-nitro-4-methoxy-5-benzyloxyphenyl)-1-propanone, m.p. 120.5°–123°, yield 65%. Reduction of this material with hydrazine hydrate and Raney nickel yielded 1-(2-amino-4-methoxy-5-benzyloxyphenyl)-1-propanone.

The latter was cyclized by treatment with formic acid and formamide to yield 6-benzyloxy-4-ethyl-7-methoxyquinoline, yield 80%, m.p. 132°–134°. Catalytic hydrogenation of the latter resulted in debenzylation to yield 4-ethyl-7-methoxyquinolin-6-ol in 85% yield, m.p. 200°–202°.

Procedure 3. 7-(OXIRANYLMETHOXY)-4-ETHYL-6-METHOXYQUINAZOLINE.—A suspension of finely powdered anhyd. K$_2$CO$_3$ in 70 ml. of DMSO containing 6.2 g. (0.03 mole) of 4-ethyl-6-methoxyquinazolin-7-ol was stirred at 25° for 15 min. Epibromohydrin (10.3 g., 0.075 mole) was added in one portion and stirring was continued for 24 hrs. at 25°, after which the mixture was poured into 800 ml. H$_2$O and extracted twice with 200 ml. EtOAc and twice with 100 ml. CH$_2$Cl$_2$. The combined organic layers were dried (anhyd. Na$_2$CO$_3$), filtered and evaporated at 100°/60 mm to afford 13.5 g. of crude yellow solid which was recrystallized from EtOAc to give 4.75 g. of the pure intermediate, m.p. 120.0°–121.0° (corr.). Elemental analysis for C, H, and N confirmed the formula C$_{14}$H$_{16}$N$_2$O$_3$.

Procedure 4. 6-(OXIRANYLMETHOXY)-4-ETHYL-7-METHOXYQUINAZOLINE.—4-Ethyl-7-methoxyquinazolin-6-ol was treated as described in Procedure 3, yield 67%, m.p. 120.0°–122.0° after recrystallization from EtOAc. Elemental analysis for C, H, and N confirmed the formula C$_{14}$H$_{16}$N$_2$O$_3$.

Procedure 5. 4-ETHYL-6,7-QUINAZOLINEDIOL.—A solution of 4-ethyl-6,7-dimethoxyquinazoline in 150 ml. of 48% HBr was refluxed for 4 hrs. and then cooled to room temperature and neutralized to pH 7 with concentrated ammonium hydroxide. The suspension was chilled overnight and the precipitate then collected on a filter and dried in the air overnight and then in a vacuum oven at 50°/60 mm for 18 hrs. The diol was then separated by fractional crystallization of 19 g. of the crude solid using first MeOH-Abs.EtOH (4:1) and then two recrystallizations from MeOH-dioxane (4:1) and a fourth crystallization from MeOH-H$_2$O by allowing the methanol to evaporate from the boiling solution until crystallization commenced. The diol was a yellow crystalline solid, yield 4.2 g., m.p. 277.0°–278.0° (dec., corr.). Elemental analysis for carbon, hydrogen, and nitrogen corresponded to the formula C$_{10}$H$_{10}$N$_2$O$_2$.

Procedure 6. 6,7-DI(OXIRANYLMETHOXY)-4-ETHYLQUINAZOLINE.—4-Ethyl-6,7-quinazolinediol when treated with epibromohydrin in the presence of potassium carbonate in DMSO as reaction medium according to the method of Procedure 3, the desired product is obtained.

The 6,7-dimethoxyquinazolines listed in the following table have been prepared by the method described in U.S. Pat. No. 3,248,292. They are suitable for conversion according to the methods of Procedures 1 and 3 to the products of Formula I wherein $R^2$ and $R^4$ have the meanings given in the table, $R^6$ is methyl and $R^7$ is oxiranylmethyl. The corrected melting points and recrystallization solvents for the quinazoline starting materials are stated.

6,7-Dimethoxyquinazolines

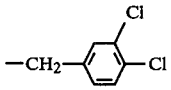

| No. | $R^2$ | $R^4$ | m.p. | Solvent | Molecular Formula |
|---|---|---|---|---|---|
| 1 | —H | —CH$_2$CH$_2$CH$_3$ | 108.5–110.5 | acetonitrile | C$_{13}$H$_{16}$N$_2$O$_2$ |
| 2 | —CH$_3$ | —CH$_2$CH$_2$CH(CH$_3$)$_2$ | 90.5–91.5 | heptane | C$_{16}$H$_{22}$N$_2$O$_2$ |
| 3 | —CH$_3$ | —CH$_2$CH$_2$CH$_3$ | 111–112.5 | isopropyl | C$_{14}$H$_{18}$N$_2$O$_2$ |
| 4 | —H | —CH(CH$_3$)$_2$ | 93–95 | isopropyl | C$_{13}$H$_{16}$N$_2$O$_2$ |
| 5 | H | H | 146–148 | ethyl acetate butanone | C$_{10}$H$_{10}$N$_2$O$_2$ |
| 6 | —H | —CH$_2$CH$_2$CH(CH$_3$)$_2$ | 79.5–81.5 | isopropyl ether | C$_{15}$H$_{20}$N$_2$O$_2$ |
| 7 | —CH$_2$CH$_2$CH$_3$ | —CH$_2$CH$_2$CH$_3$ | 157.5–159.5 | ethyl acetate | C$_{16}$H$_{22}$N$_2$O$_2$·HCl |
| 8 | —CH$_3$ | —CH$_2$CH$_3$ | 117–119 | acetonitrile isopropyl ether | C$_{13}$H$_{16}$N$_2$O$_2$ |
| 9 | —H |  | 145–146.5 | acetonitrile butanone | C$_{17}$H$_{14}$Cl$_2$N$_2$O$_2$ |
| 10 | —CH$_3$ | —CH(CH$_3$)$_2$ | 96.5–98 | isopropyl ether | C$_{14}$H$_{18}$N$_2$O$_2$ |
| 11 | H | CH$_3$ | 150–152 | acetonitrile ethyl acetate | C$_{11}$H$_{12}$N$_2$O$_2$ |
| 12 | CH$_3$ | CH$_3$ | 112–114 | acetonitrile | C$_{12}$H$_{14}$N$_2$O$_2$ |
| 13 | H | CH$_2$CH$_3$ | 146–148 | acetonitrile | C$_{12}$H$_{14}$N$_2$O$_2$ |
| 14 | H |  | 173–175 | acetonitrile | C$_{16}$H$_{14}$N$_2$O$_2$ |
| 15 | CH$_3$ | 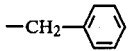 | 170–172 | ethyl acetate | C$_{17}$H$_{16}$N$_2$O$_2$ |
| 16 | H | 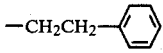 | 130–132 | acetonitrile | C$_{17}$H$_{16}$N$_2$O$_2$ |
| 17 | H | 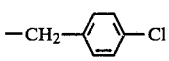 | 145–147 | acetonitrile | C$_{18}$H$_{18}$N$_2$O$_2$ |
| 18 | H | 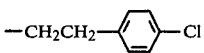 | 155–157 | acetonitrile ethanol | C$_{17}$H$_{15}$ClN$_2$O$_2$ |
| 19 | H | 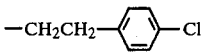 | 134–136 | acetonitrile | C$_{18}$H$_{17}$ClN$_2$O$_2$ |
| 20 | CH$_3$ | 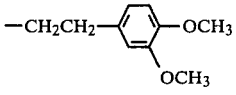 | 166–168 | acetonitrile butanone | C$_{19}$H$_{19}$ClN$_2$O$_2$ |
| 21 | H | —CH$_2$CH$_2$—⟨⟩—OCH$_3$ / OCH$_3$ | 146–148 | acetonitrile | C$_{20}$H$_{22}$N$_2$O$_4$ |
| 22 | CH$_3$ | H | 163–165 | acenotrile | C$_{11}$H$_{12}$N$_2$O$_2$ |

What is claimed is:
1. A compound having Formula I

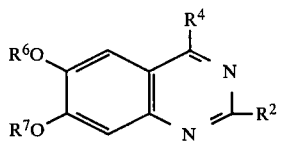

Formula I wherein one of $R^6$ and $R^7$ is oxiranylmethyl, and the other is methyl or oxiranylmethyl, and $R^2$ and $R^4$ are independently selected from the group consisting of hydrogen, alkyl having from 1 to 5 carbon atoms, phenyl, substituted phenyl, phenylalkyl having up to 8 carbon atoms, substituted phenylalkyl having up to 8 carbon atoms apart from the substituents, wherein said substituted phenyl and substituted phenylalkyl have one or two ring attached groups independently selected from halogen, methyl, or methoxy groups.

2. The compound of claim 1, 4-ethyl-6-methoxy-7-(oxiranylmethoxy)quinazoline.

3. The compound of claim 1, 4-ethyl-7-methoxy-6-(oxiranylmethoxy)quinazoline.

* * * * *